(12) United States Patent
Hoeppner et al.

(10) Patent No.: US 10,537,373 B2
(45) Date of Patent: Jan. 21, 2020

(54) POROUS IMPLANTS WITH INJECTABLE CAPABILITIES

(71) Applicant: Biomet Sports Medicine, LLC, Warsaw, IN (US)

(72) Inventors: Jacy C. Hoeppner, Warsaw, IN (US); Jason D. Meridew, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 505 days.

(21) Appl. No.: 15/136,158

(22) Filed: Apr. 22, 2016

(65) Prior Publication Data

US 2016/0310186 A1     Oct. 27, 2016

Related U.S. Application Data

(60) Provisional application No. 62/152,356, filed on Apr. 24, 2015.

(51) Int. Cl.
| | |
|---|---|
| *A61B 17/86* | (2006.01) |
| *A61B 17/80* | (2006.01) |
| *A61B 17/00* | (2006.01) |
| *A61B 17/56* | (2006.01) |

(52) U.S. Cl.
CPC ........ *A61B 17/8095* (2013.01); *A61B 17/864* (2013.01); *A61B 17/866* (2013.01); *A61B 2017/00884* (2013.01); *A61B 2017/00893* (2013.01); *A61B 2017/00955* (2013.01); *A61B 2017/561* (2013.01)

(58) Field of Classification Search
CPC .............. A61B 17/86; A61B 2017/561; A61B 2018/00065; A61B 17/8095; A61B 17/864
See application file for complete search history.

(56) References Cited

U.S. PATENT DOCUMENTS

| | | | | |
|---|---|---|---|---|
| 3,664,022 | A * | 5/1972 | Small ..................... | A61C 1/084 433/174 |
| 4,274,163 | A * | 6/1981 | Malcom ............. | A61B 17/8808 606/94 |
| 5,989,027 | A * | 11/1999 | Wagner ................ | A61C 8/0006 433/173 |
| 6,343,930 | B1 * | 2/2002 | Beaty ..................... | A61C 8/005 433/173 |
| 6,379,153 | B1 * | 4/2002 | Schroering .......... | A61C 8/0012 433/173 |

(Continued)

*Primary Examiner* — David W Bates
(74) *Attorney, Agent, or Firm* — Schwegman Lundberg & Woessner, P.A.

(57) ABSTRACT

An implant having a porous portion with a plurality of interconnected voids for receiving at least one injectable substance such that an injectable substance can elute from the porous portion. A syringe can be inserted into the at least one porous portion for administering the at least one injectable substance into the voids of the porous structure. The implant can be implanted with the at least one porous portion pre-loaded with the at least one injectable substance. The at least one porous portion can be loaded by inserting the syringe into the at least one porous portion after implanting the implant. The porous portion can be re-loaded with the syringe after the at least one injectable substance has eluted from the porous portion or replaced with a different injectable substance.

12 Claims, 5 Drawing Sheets

(56) References Cited

U.S. PATENT DOCUMENTS

| | | | | |
|---|---|---|---|---|
| 6,554,830 | B1* | 4/2003 | Chappius | A61B 17/3472 |
| | | | | 606/246 |
| 8,535,357 | B2* | 9/2013 | Stone | A61B 17/866 |
| | | | | 606/300 |
| 9,364,273 | B2* | 6/2016 | Armbruster | A61B 17/86 |
| 9,861,492 | B2* | 1/2018 | Ek | A61F 2/40 |
| 2004/0197737 | A1* | 10/2004 | Uckelmann | A61C 1/0061 |
| | | | | 433/173 |
| 2006/0036253 | A1* | 2/2006 | Leroux | A61B 17/70 |
| | | | | 623/16.11 |
| 2006/0106390 | A1* | 5/2006 | Jensen | A61B 17/8685 |
| | | | | 606/318 |
| 2007/0270858 | A1* | 11/2007 | Trieu | A61B 17/7098 |
| | | | | 606/279 |
| 2009/0005868 | A1* | 1/2009 | Gundlapalli | A61F 2/4644 |
| | | | | 623/11.11 |
| 2010/0145393 | A1* | 6/2010 | Fallin | A61B 17/866 |
| | | | | 606/301 |
| 2011/0045087 | A1* | 2/2011 | Kerr | A61N 1/3622 |
| | | | | 424/490 |
| 2011/0218644 | A1* | 9/2011 | Meridew | A61F 2/3662 |
| | | | | 623/23.15 |
| 2012/0148983 | A1* | 6/2012 | Mullen | A61C 8/0012 |
| | | | | 433/174 |
| 2012/0259365 | A1* | 10/2012 | Richelsoph | A61B 17/1671 |
| | | | | 606/247 |
| 2013/0022943 | A1* | 1/2013 | Collins | A61C 8/0012 |
| | | | | 433/174 |
| 2013/0211539 | A1* | 8/2013 | McDaniel | A61F 2/4003 |
| | | | | 623/23.53 |

* cited by examiner

POROUS IMPLANTS WITH INJECTABLE CAPABILITIES

CLAIM OF PRIORITY

This patent application claims the benefit of priority, under 35 U.S.C. Section 119(e), to Hoeppner et al. U.S. patent application Ser. No. 62/152,356, entitled "POROUS IMPLANTS WITH INJECTABLE CAPABILITIES," filed on Apr. 24, 2015, each of which is hereby incorporated by reference herein in its entirety.

TECHNICAL FIELD

This document pertains generally, but not by way of limitation, to implants configured to receive injectable substances.

BACKGROUND

During reconstructive bone surgery, an implant is secured to the bone to secure bone fragments together or replace a resected portion of the bone. The implant is configured to receive mechanical fasteners, such as screws or bolts, which can be driven into the bone to fix the implant to the bone. A drawback of a mechanical fasteners is that additional surgeries are required to remove the mechanical fasteners after the implant is secured or to remove the implant. Certain implants comprise materials for facilitating ingrowth of the surrounding bone into the implant to fuse the implant with the bone. The mechanical fasteners can interfere with the ingrowth of the bone.

In certain reconstructive surgeries, the implant can act as a bone anchor is set into the bone to provide an anchor point for sutures or other flexible elements that can be used to secure bone fragments or implants. The bone anchor can have engagement features that can be driven into the surrounding bone structure to fix the bone anchor to the bone. If the engagement features are not properly secured, the bone anchor can disengage from the bone when the suture or the flexible element is tensioned to secure the bone fragments or implants.

OVERVIEW

The present inventors have recognized, among other things, that a problem to be solved can include mechanically securing an implant to bone structure and facilitating in-growth of surrounding bone into the implant. In an example, the present subject matter can provide a solution to this problem, such as by providing an implant having at least one porous portion having a porous structure for receiving at least one injectable substance. The at least one injectable substance can elute from the porous portion onto the adjacent bone structure to fuse the implant to the bone, induce in-growth of bone or both. The injectable substance can include cement or other adhesive compounds for adhering the implant to the adjacent bone. The injectable substance can include platelet-rich plasma, concentrate bone marrow aspirate, bone marrow aspirate, blood, or combinations thereof to facilitate bone ingrowth into the porous portion to secure the bone implant to the adjacent bone structure.

In an example, the porous structure can comprise a plurality of voids for receiving the at least one injectable substance and all for bone in-growth. The porous structure can comprise a porosity of at least about 60%. In at least one example, the porous structure can comprise a porosity of at least about 70%. In certain examples, the at least one porous portion can comprise polyether-ether-ketone, polyether-ketone-ketone, or combination thereof.

In an example, the implant can comprise at least two anchor portions insertable into a bone structure to hold two adjacent bone structures together. Each anchor portion can define at least one through-hole for receiving a syringe to administer the at least one injectable substance into the corresponding anchor portion. In an example, each anchor portion can include a tip portion facilitating insertion of the anchor portion into the bone structure. The tip portion can comprise a solid structure to minimize deformation or deflection of the tip as the anchor portion is inserted into the bone structure.

In an example, the implant can be shaped as a bone anchor comprising a tip portion, a back portion, and at least one porous portion therebetween. The tip portion can comprise a solid structure to minimize deformation or deflection of the tip portion as the bone anchor is inserted into a bone structure. The back portion can comprise a solid structure for applying a push force to the bone anchor to insert the bone anchor into the bone structure. In at least one example, the bone anchor can comprise a threaded engagement feature such that the bone anchor can be rotated into engagement with the bone structure. In this configuration, the back portion can be configured to be griped or engaged to rotate the bone anchor into the bone structure.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
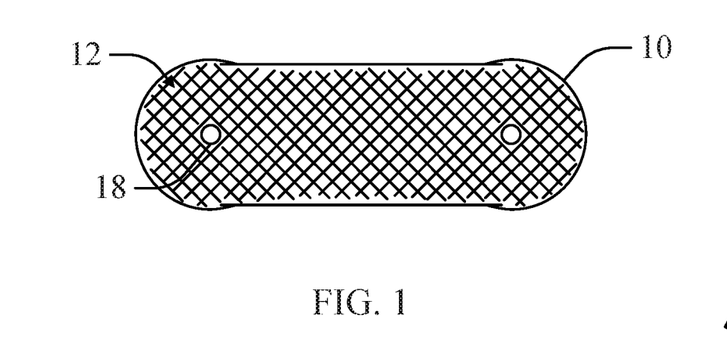
FIG. 1 is a top view of an implant in a bone stable configuration according to an example of the present disclosure.
Figure 2:
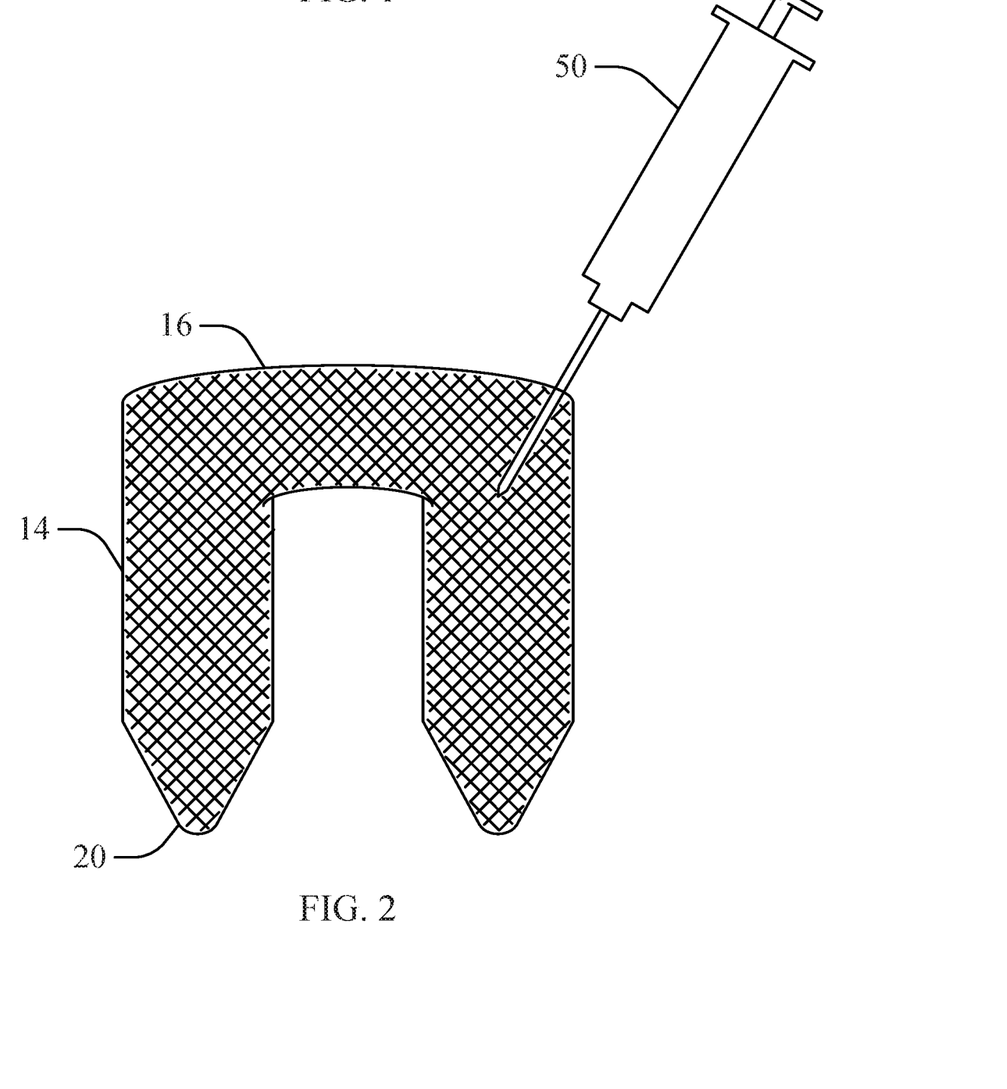
FIG. 2 is a front view of the implant depicted in FIG. 1, wherein a syringe administering at least one injectable substance according to an example of the present disclosure.

As depicted in FIGS. 1-2, an implant 10, according to an example of the present disclosure, can comprise at least one porous portion 12. The porous portion 12 can comprise a porous structure having a plurality of interconnected voids for receiving at least one injectable substance such that the at least one injectable substance can elute from the porous portion 12. In an example, a syringe 50 can be inserted into the at least one porous portion 12 for administering the at least one injectable substance into the voids of the porous structure. The implant 10 can be implanted with the at least one porous portion 12 pre-loaded with the at least one injectable substance. In an example, the at least one porous portion 12 can be loaded by inserting the syringe 50 into the at least one porous portion 12 after implanting the implant 10. The porous portion 12 can be re-loaded with the syringe 50 after the at least one injectable substance has eluted from the porous portion 12 or replaced with a different injectable substance.

In an example, the at least one injectable substance can elute from the at least one porous portion 12 onto the adjacent bone structure to fuse the implant 10 to the bone, induce in-growth of bone, supplying nutrients, or combinations thereof. The at least one injectable substance can include cement or other adhesive compounds for adhering the implant 10 to the adjacent bone. The at least one injectable substance can include platelet-rich plasma, concentrate bone marrow aspirate, bone marrow aspirate, blood, or combinations thereof to facilitate bone ingrowth into the at least one porous portion 12 to secure the implant 10 to the adjacent bone structure.

In an example, the porous portion 12 can be a highly porous, three-dimensional structure including a large plurality of ligaments that define open voids (e.g., pores) or channels between the ligaments for receiving the at least one injectable substance and all for bone in-growth. The open spaces between the ligaments can form a matrix of continuous channels having few or no dead ends, such that growth of soft tissue and/or bone through the open porous structure is substantially uninhibited. Such structures can be particularly suited for contacting bone and/or soft tissue, and in this regard, can be useful as bone substitutes and other implants and implant components that are receptive to cell and tissue ingrowth or mineralization, for example, by allowing bony tissue or other tissue to grow into the porous structure over time to enhance fixation (e.g., osseointegration) between the structure and surrounding bodily structures. According to some aspects of the present disclosure, exterior surfaces of an open porous structure can feature terminating ends of the above-described ligaments. Such terminating ends can be referred to as struts, and they can generate a high coefficient of friction along an exposed porous surface. Such features can impart an enhanced affixation ability to an exposed porous surface for adhering to bone and soft tissue. The at least one porous portion 12 can comprise one or more of a variety of biocompatible materials such as, but not limited to polyether-ether-ketone, polyether-ketone-ketone, or combination thereof.

Such structures can be isotropic or anisotropic. In this regard, according to certain examples, an open porous structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. According to certain examples of the present disclosure, an open porous structure, or a portion thereof, may have a bulk porosity as low as 55%, 65%, or 75% or as high as 80%, 85%, or 90%, or within any range defined between any pair of the foregoing values, and in this regard, such structures can provide lightweight, yet strong porous implants. In an example, the porous structure can comprise a bulk porosity of at least 60%. In at least one example, the porous structure can comprise a bulk porosity of at least about 70%. Also, when such highly porous structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

Such structures can be manufactured according to any suitable technique or process. In certain examples, a highly porous, three-dimensional structure will be fabricated using a selective laser sintering (SLS) or other additive manufacturing-type process such as direct laser sintering or electron beam melting. In an example, a three-dimensional porous article is produced in layer-wise fashion from a laser-fusible powder, e.g., a single-component polymer powder, which can be deposited one layer at a time. The powder can be fused, re-melted or sintered, by the application of laser energy that is directed to portions of the powder layer corresponding to a cross section of the article. After the fusing of the powder in each layer, an additional layer of powder can be deposited, and a further fusing step can be carried out, with fused portions or lateral layers fusing so as to fuse portions of previous laid layers until a three-dimensional article is complete. In certain examples, a laser can selectively fuse powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In certain examples, a non-porous or essentially non-porous portion of an otherwise porous article also can be made using a selective laser sintering (SLS) or other additive manufacturing-type process.

As depicted in FIGS. 1-2, in an example, the implant 10 can comprise a bone staple for anchoring two bone structures together. The implant 10 having at least two anchor portion 14 joined by the bridge portion 16. Each anchor portion 14 can be inserted to a bone structure such that adjacent bone structures are held together by the bridge portion 16. Each anchor portion 14 can comprise at least one porous portion 12 such that the at least one injectable substance elutes into the corresponding bone structure. In an example, each anchor portion 14 can comprise a through-hole 18 for receiving a syringe 50 to administer the injectable substance into the porous portion 12. Each anchor portion 14 can include a tip portion 20, which can be shaped to facilitate the insertion of the anchor portion 14 into the bone structure. In an example, the tip portion 20 can comprise a solid structure to minimize deformation or deflection of the tip portion 20 as the anchor portion 14 is inserted into the bone structure.

Figure 3:
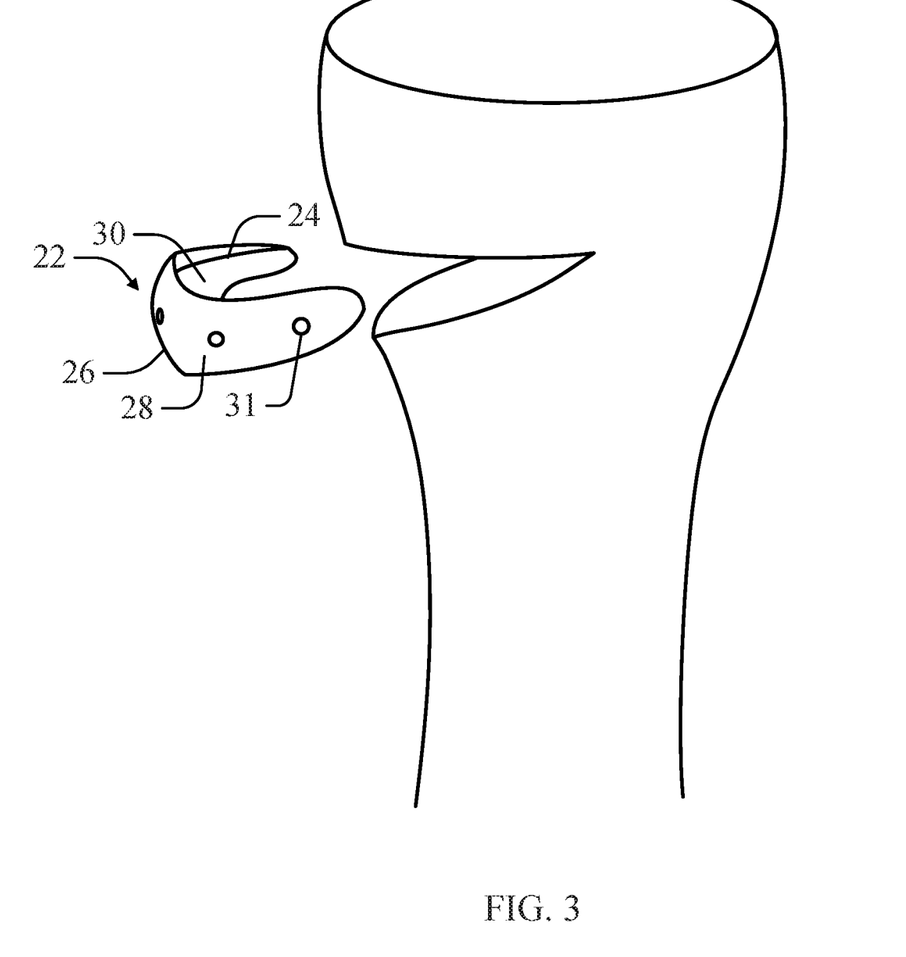
FIG. 3 is a schematic view of an implant in a reconstructive insert configuration being inserted into a resected bone space according to an example of the present disclosure.

As depicted in FIG. 3, in an example, an implant 22 can comprise a reconstructive insert for performing fusions or osteotomies. The implant 22 can comprise at least one porous portion 24 and at least one solid portion 26. The solid portion 26 can be arranged around the at least one porous portion 24 such that the solid portion 26 defining an exterior surface 28 of the implant 22. In this configuration, the solid portion 26 provides a rigid or semi-rigid exterior surface 28 aligning with an exterior surface of the bone structure. The solid portion 26 can also provide structural support preventing the at least one porous portion 24 or cutout portion in the bone structure from collapsing. The at least one porous portion 24 can define at least one interior surface 30 for engaging a prepared bone surface such that the at least one injectable substance elutes from the at least one porous portion 24 on the prepared bone surface. In an example, the solid portion 26 can include at least one through-hole 31 for receiving a syringe to administer the injectable substance into the porous portion 24.

Figure 4:
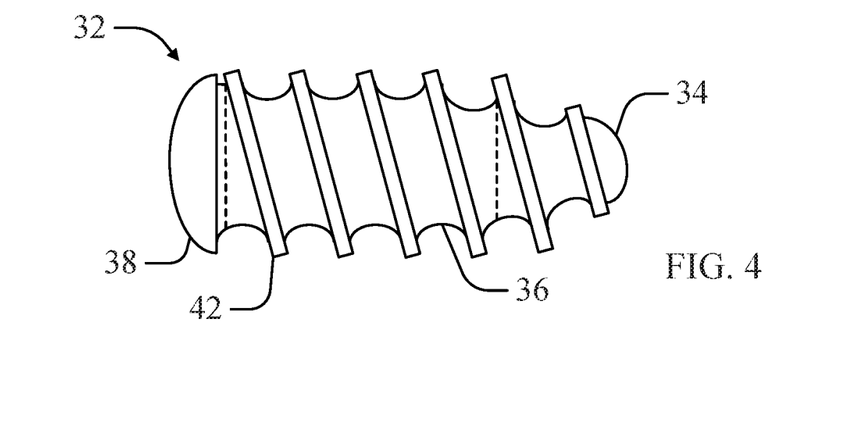
FIG. 4 is a side view of an implant in a bone anchor configuration according to an example of the present disclosure.
Figure 5:
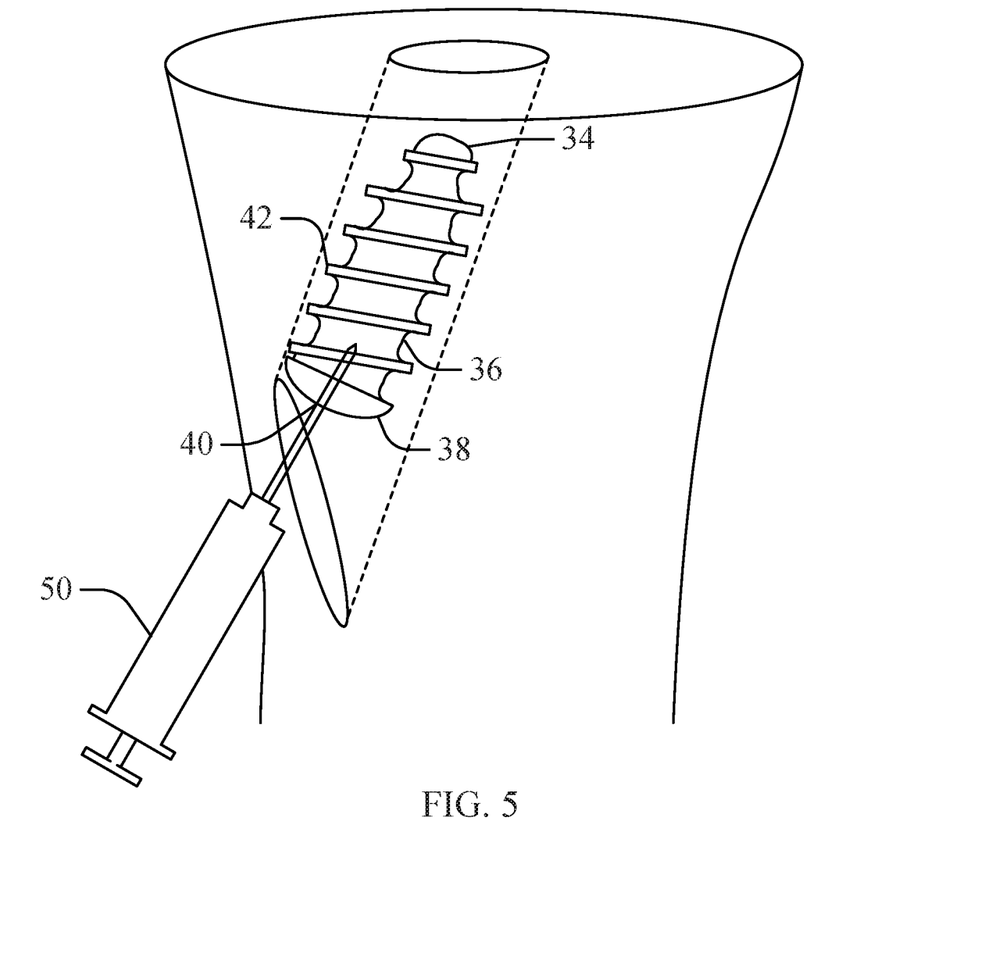
FIG. 5 is a schematic view of the implant depicted in FIG. 4, wherein the bone anchor is being inserted into a bore hole in the bone structure.
Figure 6:
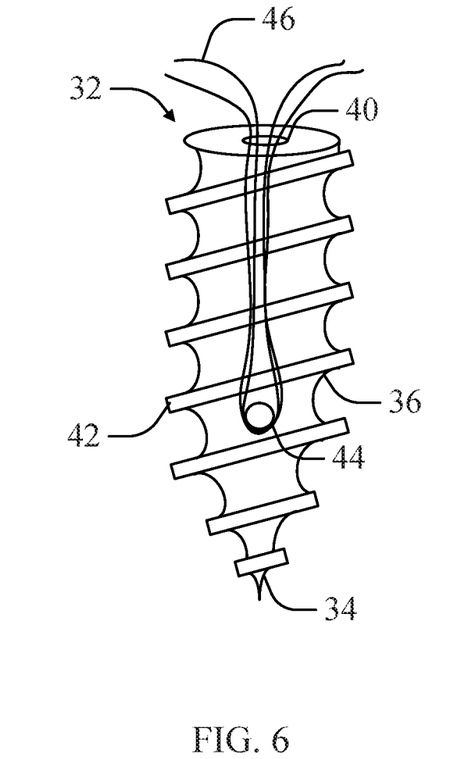
FIG. 6 is a side view of an implant in a bone anchor configuration according to an example of the present disclosure.

As depicted in FIGS. 4-6, in an example, an implant 32 can comprise a bone anchor that can be secured within the bore hole in the bone structure. The implant 32 can comprise a tip portion 34, at least one porous portion 36, and rear portion 38 where the at least one porous portion 36 is positioned between the tip portion 34 and the rear portion 38. In an example, a through hole 40 can extend through the rear portion 38 of the implant 32 to facilitate insertion of a syringe 50 through the rear portion 38 and into the at least one porous portion 36. The tip portion 34 can comprise a solid structure to minimize deformation or deflection of the tip portion 34 as the implant 32 is inserted into the bore hole. As depicted in FIGS. 4-5, in an example, the tip portion 34 can be rounded. As depicted in FIG. 6, in an example, the tip portion 34 can be pointed to facilitate insertion into the bore hole.

As depicted in FIGS. 4-6, in an example, the implant 32 can comprise a threaded engagement feature 42 that can be rotatably engaged to the surrounding surface of the bore hole. The rear portion 38 can comprise a solid structure such that the rear portion 38 can be gripped or engaged by a screw driver or other tool to rotate the implant 32 to engage the threaded engagement feature 42 into the surrounding surface of the bore hole. As depicted in FIG. 6, in an example, the implant 32 can include a suture anchor 44 permitting a suture 46 to be threaded through the through-hole 40. The suture anchor 44 can be positioned in the rigid tip portion 34 or in the porous portion 36.

Figure 7:
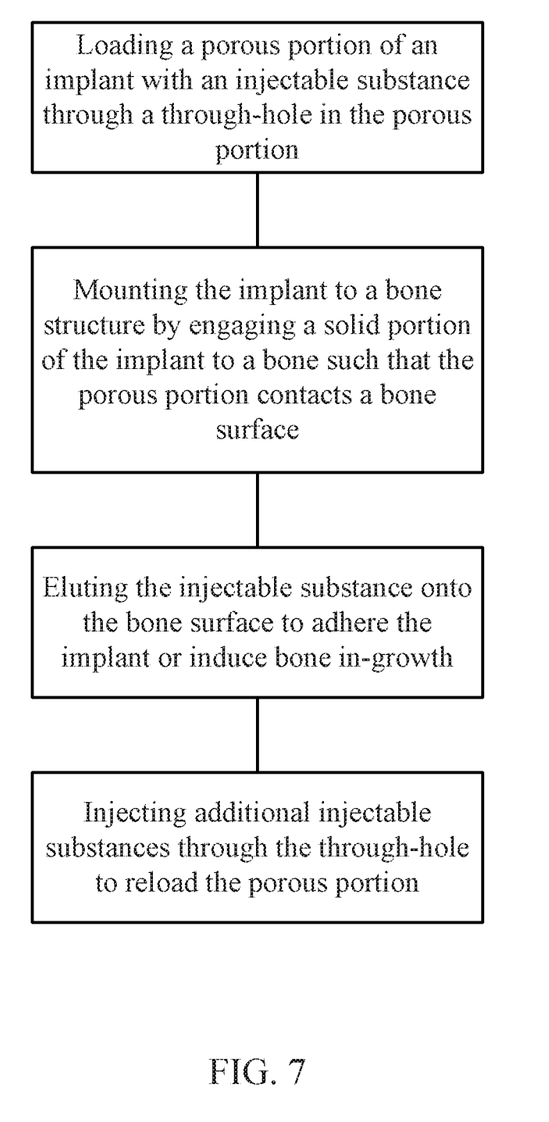
FIG. 7 is a schematic view of a method of implanting according to an example of the present disclosure.

As depicted in FIG. 7, in an example, a method for implanting an implant 10 within a bone structure can comprise a loading step, an implantation step, and an eluting step.

The loading step can include administering at least one injectable substance into at least one porous portion 12 of the implant 10 with a syringe 50. The loading step can be performed prior to the implantation step. In an example, the loading step can be performed after the implantation step such that the at least one injectable substance is directly applied to the bone surface through the porous portion 12.

The implantation step can include insertion of the implant 10 into bone structure. In an example, the at least one porous portion 12 can be positioned against a bone surface to which the implant 10 is to be mounted or against a prepared bone surface of resected portion of the bone structure. A solid portion 14 of the implant 10 can be engaged to the bone structure to position the porous portion 12 against the bone surface.

The eluting step can include elution of the at least one injectable substance from the at least one porous portion 12 on the mounting bone surface or prepared bone surface of the bone structure. The at least one injectable substance can adhere the implant 10 to the bone surface or induce ingrowth of bone into the at least one porous portion 12.

In an example, the method can include a reloading step where the syringe 50 is reinserted into the porous portion 12 to replace the at least one injectable substance that has eluted from the at least one porous portion or supply a different injectable substance to induce reaction between the implant 10 and the bone surface.

VARIOUS NOTES & EXAMPLES

Example 1 is an implant, comprising: an implant body comprising at least one porous portion and a solid portion for mounting the implant body; wherein the at least one porous portion having a porous structure for receiving at least one injectable substance.

In Example 2, the implant of Example 1 optionally includes, wherein the at least one porous portion defines at least one through-hole sized to receive a syringe for injecting the at least one injectable substance into the porous structure.

In Example 3, the implant of Example 2 optionally includes, wherein the at least one through-hole extends through the porous structure for distributing the at least one injectable substance throughout the porous structure.

In Example 4, the implant of any one or more of Examples 1-3 optionally include, wherein the porous portion comprises a porosity of at least about 60%.

In Example 5, the implant of any one or more of Examples 1-4 optionally include, wherein the porous portion comprises at least one of polyether ether ketone and polyether ketone ketone.

In Example 6, the implant of any one or more of Examples 1-5 optionally include, wherein the implant body comprises at least one solid portion; wherein the solid portion comprises a solid non-porous structure.

In Example 7, the implant of Example 6 optionally includes, wherein the solid portion comprises solid polyether ketone ketone.

In Example 8, the implant of any one or more of Examples 6-7 optionally include, wherein the at least one solid portion is arranged around the at least one portion such that the at least one solid portion defines an exterior surface of the implant body.

In Example 9, the implant of Example 8 optionally includes, wherein the at least one porous portion defines an interior surface of the implant body for interfacing with a bone surface.

In Example 10, the implant of any one or more of Examples 6-9 optionally include, wherein solid portion defines at least one injection port extending through the solid portion permitting the at least one injectable substance to pass through the solid portion.

In Example 11, the implant of any one or more of Examples 1-10 optionally include, wherein the implant body comprises at least two anchor portions, each anchor portion engagable to a bone structure for operably connecting two adjacent bone structures.

In Example 12, the implant of any one or more of Examples 1-11 optionally include, wherein the implant body comprises a threaded engagement feature such that the implant body can be screwed into a bone structure.

In Example 13, the implant of Example 12 optionally includes, wherein the implant body comprises: a tip portion; and a back portion, wherein the tip portion and the back portion comprises a solid non-porous structure; wherein the at least one porous portion is positioned between the tip portion and the back portion.

In Example 14, the implant of any one or more of Examples 1-13 optionally include, wherein the at least one injectable substance comprises at least one of platelet-rich plasma, concentrated bone marrow aspirate, bone marrow aspirate, blood, and cement.

Example 15 is a method of repairing a bone structure, comprising: providing an implant body comprising at least one porous portion having a porous structure; injecting at least one injectable substance into the porous portion; and implanting the implant body into the bone structure such that the at least one injectable substance elutes from the porous portion.

In Example 16, the method of Example 15 optionally includes, wherein the implant body is implanted into the bone structure prior to injection of the at least one injectable substance such that the at least one injectable substance elutes from the porous portion into contact with the bone structure.

In Example 17, the method of any one or more of Examples 15-16 optionally include, wherein the at least one porous portion defines at least one through-hole sized to receive a syringe for injecting the at least one injectable substance into the porous structure.

In Example 18, the method of any one or more of Examples 15-17 optionally include, wherein the implant body further comprises at least one solid portion arranged around the at least one porous portion and defining an exterior surface of the implant body; wherein the exterior surface interfaces with the bone structure upon implantation of the implant body.

In Example 19, the method of Example 18 optionally includes, wherein the solid portion defines at least one injection port extending through the solid portion permitting the at least one injectable substance to pass through the solid portion.

Example 20 is a system for repairing a bone structure, comprising: an implant body comprising at least one porous portion, wherein the at least one porous portion having a porous structure; and a syringe containing at least one injectable substance; wherein the syringe is configured to inject the at least one injectable substance into the porous structure of the porous portion.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. An implant, comprising:
   an implant body comprising at least one porous portion and a solid portion for mounting the implant body to a bone structure; and
   at least one injectable substance pre-loaded into the implant body prior to completion of mounting the implant body to a bone structure, wherein the at least one injectable substance comprises at least one of platelet-rich plasma, concentrated bone marrow aspirate, bone marrow aspirate, or blood;
   wherein the implant body comprises a threaded engagement feature such that the implant body can be screwed into a bone structure;
   wherein the at least one porous portion comprises a highly porous three-dimensional structure including a plurality of ligaments that define open voids between the ligaments for receiving the at least one injectable substance and allowing for bone in-growth, the open voids between the ligaments forming a matrix of continuous channels having few or no dead ends such that growth of soft or bony tissue through the three-dimensional structure is substantially uninhibited;
   wherein the highly porous three-dimensional structure comprises a bulk porosity of at least 55 %;
   wherein the solid portion defines at least one injection port extending through the solid portion; and
   wherein the at least one porous portion defines at least one hole in fluid communication with the at least one injection port and sized to receive a syringe for injecting the at least one injectable substance into the highly porous three-dimensional structure, the at least one hole extending into the highly porous three-dimensional structure for distributing the at least one injectable substance through the open voids.

2. The implant of claim 1, wherein the porous portion comprises a porosity of at least 60%.

3. The implant of claim 1, wherein the porous portion comprises at least one of polyether ether ketone and polyether ketone ketone.

4. The implant of claim 1, wherein the solid portion comprises a solid non-porous structure.

5. The implant of claim 4, wherein the solid portion comprises solid polyether ketone ketone.

6. The implant of claim 4, wherein the at least one solid portion is arranged around the at least one porous portion such that the at least one solid portion defines an exterior surface of the implant body.

7. The implant of claim 6, wherein the at least one porous portion defines an interior surface of the implant body for interfacing with a bone surface.

8. The implant of claim 1, wherein the solid portion of the implant body comprises a solid non-porous structure, the solid non-porous structure including:
   a tip portion; and
   a back portion;
   wherein the at least one porous portion is positioned between the tip portion and the back portion.

9. A system for repairing a bone structure, comprising:
   a wedge-shaped implant body configured for use in an osteotomy procedure comprising a solid base portion and a tapered porous portion extending from the solid base portion and defining a decreasing thickness of the wedge-shaped implant body, the tapered porous portion comprising a highly porous three-dimensional structure defined by a bulk porosity of at least 55% and including a plurality of ligaments that define open voids between the ligaments for receiving at least one injectable substance and allowing for bone in-growth, the solid base portion arranged relative to the tapered porous portion such that the solid base portion defines a rigid exterior surface of the wedge-shaped implant body configured to align with an exterior surface of the bone structure, the solid base portion defining a plurality of injection ports spaced apart along the rigid exterior surface of the wedge-shaped implant body that are in fluid communication with the tapered porous portion, and the tapered porous portion defining an interior surface of the wedge-shaped implant body configured to engage a prepared bone surface of the bone structure such that the at least one injectable substance can elute from the tapered porous portion onto the prepared bone surface; and
   a syringe containing the at least one injectable substance, the syringe configured to inject the at least one injectable substance into the highly porous three-dimensional structure of the tapered porous portion.

10. The system of claim 9, wherein the porous portion defines at least one hole in fluid communication with the at least one injection port and sized to receive the syringe for injecting the at least one injectable substance into the highly porous three-dimensional structure, the at least one hole extending into the highly porous three-dimensional structure for distributing the at least one injectable substance through the open voids.

11. An implant, comprising:
   an implant body comprising at least one porous portion and a solid portion for mounting the implant body to a bone structure;
   wherein the at least one porous portion comprises a highly porous three-dimensional structure including a plurality of ligaments that define open voids between the ligaments for receiving at least one injectable substance and allowing for bone in-growth, the open voids between the ligaments forming a matrix of continuous channels having few or no dead ends such that growth of soft or bony tissue through the three-dimensional structure is substantially uninhibited;
   wherein the highly porous three-dimensional structure comprises a bulk porosity of at least 55%;
   wherein the implant comprises a bone staple, and wherein the implant body comprises at least two anchor portions joined by a bridge portion, each anchor portion engagable to a bone structure for operably connecting two adjacent bone structures;
   wherein the solid portion defines at least one injection port extending through the solid portion; and
   wherein the at least one porous portion defines at least one hole in fluid communication with the at least one injection port and sized to receive a syringe for injecting the at least one injectable substance into the highly porous three-dimensional structure, the at least one hole extending into the highly porous three-dimensional structure for distributing the at least one injectable substance through the open voids.

12. An implant, comprising:
   an implant body comprising at least one porous portion and a solid portion for mounting the implant body to a bone structure, the solid portion comprising a solid non-porous structure that is arranged around the at least one porous portion such that the solid portion defines an exterior surface of the implant body; and
   at least one injectable substance pre-loaded into the implant body prior to completion of mounting the implant body to a bone structure, wherein the at least one injectable substance comprises at least one of platelet-rich plasma, concentrated bone marrow aspirate, bone marrow aspirate, or blood;
   wherein the at least one porous portion comprises a highly porous three-dimensional structure including a plurality of ligaments that define open voids between the ligaments for receiving the at least one injectable substance and allowing for bone in-growth, the open voids between the ligaments forming a matrix of continuous channels having few or no dead ends such that growth of soft or bony tissue through the three-dimensional structure is substantially uninhibited;
   wherein the highly porous three-dimensional structure comprises a bulk porosity of at least 55%;
   wherein the solid portion defines at least one injection port ending through the solid portion; and
   wherein the at least one porous portion defines at least one hole in fluid communication with the at least one injection port and sized to receive a syringe for injecting the at least one injectable substance into the highly porous three-dimensional structure, the at least one hole extending into the highly porous three-dimensional structure for distributing the at least one injectable substance through the open voids.

* * * * *

UNITED STATES PATENT AND TRADEMARK OFFICE
CERTIFICATE OF CORRECTION

PATENT NO. : 10,537,373 B2
APPLICATION NO. : 15/136158
DATED : January 21, 2020
INVENTOR(S) : Hoeppner et al.

It is certified that error appears in the above-identified patent and that said Letters Patent is hereby corrected as shown below:

In the Claims

In Column 10, Line 54, in Claim 12, delete "ending" and insert --extending-- therefor Signed and Sealed this
Fourteenth Day of July, 2020

Andrei Iancu
*Director of the United States Patent and Trademark Office*